United States Patent
Laut et al.

(10) Patent No.: US 8,348,095 B2
(45) Date of Patent: Jan. 8, 2013

(54) COUNTER FOR A DEVICE FOR DISPENSING A FLUID OR POWDER PRODUCT

(75) Inventors: Antoine Laut, Etrepagny (FR); Lila Graine, Beynes (FR)

(73) Assignee: Aptar France SAS, Le Neubourg (FR)

( * ) Notice: Subject to any disclaimer, the term of this patent is extended or adjusted under 35 U.S.C. 154(b) by 12 days.

(21) Appl. No.: 13/142,755

(22) PCT Filed: Dec. 28, 2009

(86) PCT No.: PCT/FR2009/052707
§ 371 (c)(1),
(2), (4) Date: Jun. 29, 2011

(87) PCT Pub. No.: WO2010/076530
PCT Pub. Date: Jul. 8, 2010

(65) Prior Publication Data
US 2012/0012612 A1    Jan. 19, 2012

(30) Foreign Application Priority Data
Dec. 30, 2008 (FR) ..................................... 08 59153

(51) Int. Cl.
*B67D 7/22* (2010.01)
(52) U.S. Cl. ..................................... 222/36; 128/205.23
(58) Field of Classification Search .............. 222/36–38, 222/47–49; 128/205.23, 203.15, 203.12, 128/200.11–200.24; 116/309, 311–318; 215/230
See application file for complete search history.

(56) References Cited

U.S. PATENT DOCUMENTS

| | | | | |
|---|---|---|---|---|
| 6,283,365 | B1 * | 9/2001 | Bason | 235/116 |
| 6,659,307 | B1 * | 12/2003 | Stradella | 222/23 |
| 7,322,352 | B2 * | 1/2008 | Minshull et al. | 128/203.15 |

(Continued)

FOREIGN PATENT DOCUMENTS
FR        2 857 769 A1        1/2005
(Continued)

OTHER PUBLICATIONS

International Preliminary Report on Patentability issued on Aug. 2, 2011 in counterpart application PCT/FR2009/052707.

*Primary Examiner* — Lien Ngo
(74) *Attorney, Agent, or Firm* — Sughrue Mion, PLLC

(57) ABSTRACT

A dose counter for a fluid dispenser device, said counter including a first rotary counter element (410) forming a units wheel, and a second rotary counter element (420) forming a tens wheel, said first counter element (410) co-operating with an actuator member (430) that is adapted to cause said first counter element (410) to turn each time said actuator member (430) is actuated, said first rotary counter element (410) including means (418, 419) that are adapted to cause said second counter element (420) to turn on every tenth actuation of said actuator member (430), said actuator member (430) including an opening that is mounted in rotary manner on said pivot pin (461), a substantially rigid and substantially rectilinear tab (431) extending radially from said opening, said tab (431) co-operating with the first counter element (410) on each actuation, said tab (431) being extended on the other side of said pivot pin by a substantially rigid and substantially rectilinear portion, that is itself connected to an elastically-deformable portion (434) of shape that is curved and that passes, at least in part, around the pivot pin (461).

13 Claims, 4 Drawing Sheets

U.S. PATENT DOCUMENTS

| | | | |
|---|---|---|---|
| 7,387,122 B2 * | 6/2008 | Nishibayashi et al. | 128/203.15 |
| 7,766,188 B2 * | 8/2010 | Pocock et al. | 222/36 |
| 8,113,199 B2 * | 2/2012 | Augustyn et al. | 128/205.23 |
| 8,186,343 B2 * | 5/2012 | Stradella et al. | 128/200.14 |
| 8,245,906 B2 * | 8/2012 | Crosby et al. | 235/91 R |
| 2004/0255936 A1 * | 12/2004 | Urbanus | 128/200.23 |
| 2008/0041877 A1 | 2/2008 | Stradella et al. | |

FOREIGN PATENT DOCUMENTS

| | | |
|---|---|---|
| WO | 2005/079727 A2 | 9/2005 |
| WO | 2008/079360 A2 | 7/2008 |

* cited by examiner

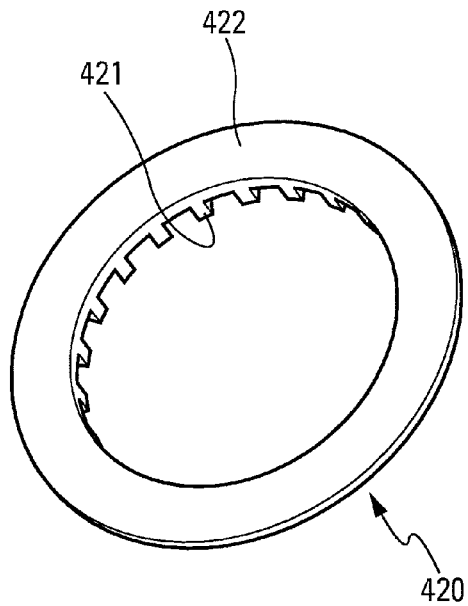
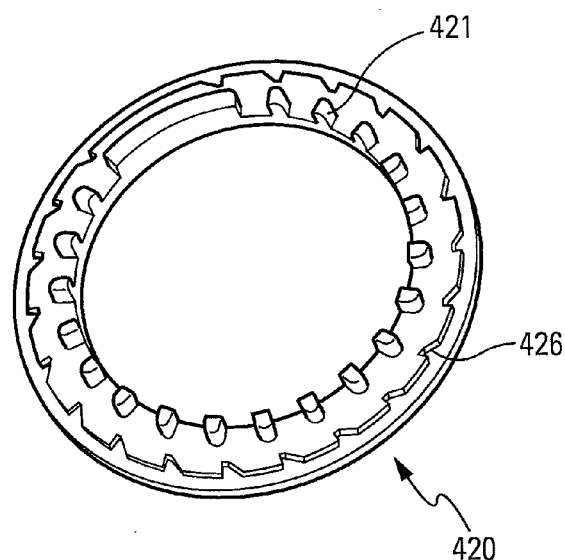
Fig. 7a　　　　　　Fig. 7b
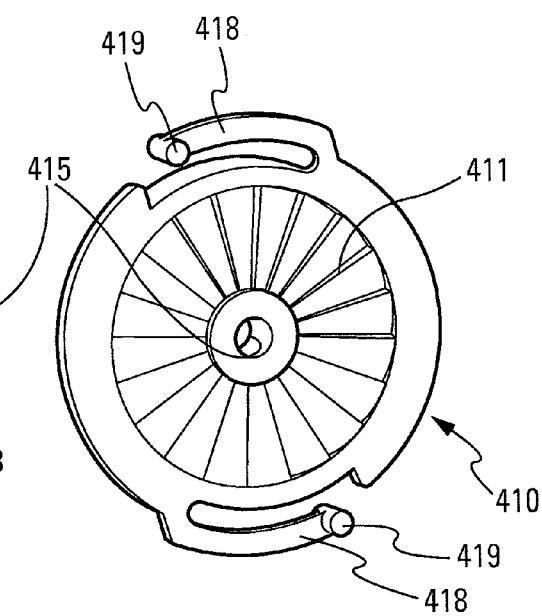
Fig. 8a　　　　　　Fig. 8b

COUNTER FOR A DEVICE FOR DISPENSING A FLUID OR POWDER PRODUCT

CROSS REFERENCE TO RELATED APPLICATIONS

This application is a National Stage of International Application No. PCT/FR2009/052707 filed Dec. 28, 2009, claiming priority based on French Patent Application No. 0859153 filed Dec. 30, 2008, the contents of all of which are incorporated herein by reference in their entirety.

The present invention relates to a counter, and more particularly to a dose counter, for indicating to the user the number of doses that have been dispensed or that remain to be dispensed from a fluid or powder dispenser device.

The use of counters or of indicators is well known in the field of fluid dispensers, in particular in the field of pharmaceuticals. In particular, such counters or indicators are used with dispenser devices of the metered dose inhaler (MDI) type, in which a reservoir containing fluid and a propellant gas is movably mounted in a body, movement of said reservoir actuating a metering valve mounted on said reservoir, so as to dispense a dose of fluid. A first family of counters envisages fastening the counter on the bottom of the reservoir, projecting out from the body, and on which the user presses in order to dispense a dose. However, that type of counter presents the drawback of interfering with the actuation of the dispenser device, with it being necessary for the user to press on the counter in order to actuate the device. In the event of poorly controlled or partial actuation, problems of over- and/or under-counting and/or of incomplete or faulty dispensing may thus occur. A second family of counters comprises counters that are disposed inside the body, being fastened either to the body or to the movable reservoir in said body. In particular, that type of counter presents the drawback of a complex mounting, and requires substantial modifications to the various component parts of the dispenser device. The assembly problem occurs in particular when assembly is performed by the manufacturer of the pharmaceutical, as opposed to by the manufacturer of the dispenser device, with that requiring the manufacturer of the pharmaceutical to install complex assembly machines in its own factory. A third family of counters envisages arranging the counter on an outside face of the body, a projection of said counter passing through an opening in the body, so as to co-operate with the reservoir or a portion that is secured to said reservoir. That type of counter also generally requires substantial modification to the body in order to receive the counter. In addition, the presence of a counter on the outside main face of the body substantially modifies the external appearance of the device, in particular because of the thickness of said counter, and that may also have a negative effect on the handling of the device. In addition, the counters used on dispenser devices for dispensing fluids, in particular pharmaceuticals, need to comply with several constraints. Thus, in order to avoid any risk of under-counting, it is generally required that the counter is actuated at the very beginning of the actuation stroke of the valve or the pump, so as to avoid partial actuation, causing a partial or complete dose to be dispensed without any dose being counted by the counter. In this situation, a problem that occurs is that the actuation stroke is generally very short, and that the manufacturing tolerances of the device tend to reduce even further the distance available to perform the actuation in effective manner. The use of a complex mechanism is generally required in order to provide counting that is functional and safe. In general, assembling counters, in particular counters including a plurality of rotary elements that are interleaved in one another, is found to be complex and thus not only costly, but also a source of malfunctions.

An object of the present invention is to provide a counter, more particularly a dose counter, for a fluid or powder dispenser device, that does not reproduce the above-mentioned drawbacks.

In particular, an object of the present invention is to provide such a counter that presents minimum thickness.

Another object of the present invention is to provide such a counter that can be pre-assembled prior to being delivered to the manufacturer of the pharmaceutical, said manufacturer thus needing only to perform a single step of mounting the counter on the body of the dispenser device, without any complex assembly of the component parts of said counter.

Another object of the present invention is to provide such a counter that guarantees actuation of the counter independently of the length of the actuation stroke of the pump or of the valve used in the device.

Another object of the present invention is to provide such a counter that is simpler and thus less costly to manufacture and to assemble, and that is more reliable in operation.

The present invention thus provides a dose counter for counting the number of doses of fluid or powder that have been dispensed or that remain to be dispensed from a fluid dispenser device, said counter including a first rotary counter element forming a units wheel, and a second rotary counter element forming a tens wheel, said first and second counter elements co-operating with each other to define said number of doses, said first counter element co-operating with an actuator member that is adapted to cause said first counter element to turn each time said actuator member is actuated, said first rotary counter element including means that are adapted to cause said second counter element to turn on every tenth actuation of said actuator member, said first and second counter elements turning about a common pivot pin, said actuator member including an opening that is mounted in rotary manner on said pivot pin, a substantially rigid and substantially rectilinear tab extending radially from said opening, said tab supporting a lug that is adapted to co-operate with the first counter element on each actuation, said tab being extended on another side of said pivot pin by a substantially rigid and substantially rectilinear portion that extends radially from said opening, and that is connected to an elastically-deformable portion of shape that is curved and that passes, at least in part, around the pivot pin, said deformable portion being extended by a support portion that is substantially rigid and that supports an actuator element, such that, on each actuation, said actuator element is moved in translation and transmits this traction force to said elastically-deformable curved portion, causing said rectilinear portion and said tab to turn about said pivot pin.

Advantageously, abutment means define the maximum turning amplitude of said tab.

Advantageously, said support portion that supports the actuator element is substantially U-shaped, the two branches of the U shape surrounding said tab.

Advantageously, the actuator member includes a resilient blade that co-operates with a projection so as to form resilient return means that return the actuator member into its rest position, after each actuation.

Advantageously, the flexibility of said resilient blade is greater than the flexibility of said elastically-deformable curved portion, such that, during actuation, the actuator member firstly turns around the pivot pin, so as to cause the first counter element to turn, and then the actuator element is free to continue its axial movement by means of said elastically-deformable portion deforming.

Advantageously, the counter includes a base body that incorporates the pivot pin and an opening.

Advantageously, said base body includes fastener means, such as snap-fastener tabs, for holding the actuator member and the first and second counter elements assembled on said base body, said counter possibly being pre-assembled so as to form a counter unit, said counter unit including fastener means for fastening to a body of a fluid dispenser device.

Advantageously, the counter comprises: a first rotary counter element provided with a first peripheral edge portion including counter indices, such as one or more series of numbers from 0 to 9, in particular two series of numbers from 0 to 9, distributed over said periphery, and provided with a first set of teeth; a second rotary counter element provided with a second peripheral edge portion including counter indices, such as numbers from 00 to 20, distributed over said periphery, and provided with a second set of teeth and with a third set of teeth; and a movable actuator member that is movable between a first position and a second position, said actuator member including a tab that is adapted to co-operate with said first set of teeth of said first counter element, so as to cause said first counter element to turn when said actuator element is moved from its first position to its second position; said first counter element including at least one deformable finger that is movable between a non-deformed position and a deformed position, which deformable finger is adapted, in its deformed position, to co-operate with said second set of teeth of said second counter element, so as to cause said second counter element to turn; said counter including a base body that supports said actuator member and said first and second counter elements, said base body including a cam that is adapted to deform said at least one deformable finger towards its deformed position.

Advantageously, said second peripheral edge portion of said second counter element is coplanar with, and radially outside, said first peripheral edge portion of said counter element, said first and second counter elements having a common axis.

Advantageously, said first rotary counter element includes two deformable fingers that are diametrally opposite each other on said first counter element.

Advantageously, said first counter element is a disk, said deformable fingers being disposed at 180° from each other and co-operating with a cam that is disposed radially on the outside of said disk, so that when a deformable finger co-operates with said cam, it is deformed radially inwards into its deformed position, so as to come into engagement with said second set of teeth of said second counter element.

The present invention also provides a fluid or powder dispenser device comprising a reservoir, a dispenser member, such as a metering valve, that is mounted on said reservoir, and a body incorporating a dispenser orifice, said reservoir being movable in said body so as to dispense the fluid or powder, said dispenser device including a counter as described above.

Advantageously, said counter is fastened on a face of the body, said device being actuated by the user pressing axially on the reservoir, and said counter being actuated by said axial movement of said reservoir that co-operates with said actuator element of the actuator member.

These characteristics and advantages and others of the present invention appear more clearly from the following detailed description, given by way of non-limiting example, and with reference to the accompanying drawings, in which:

FIGS. 7a and 7b are diagrammatic front and rear views respectively of the second rotary counter element, in an advantageous variant embodiment; and FIGS. 8a and 8b are diagrammatic front and rear views respectively of the first rotary counter element, in an advantageous variant embodiment.

Figure 1:
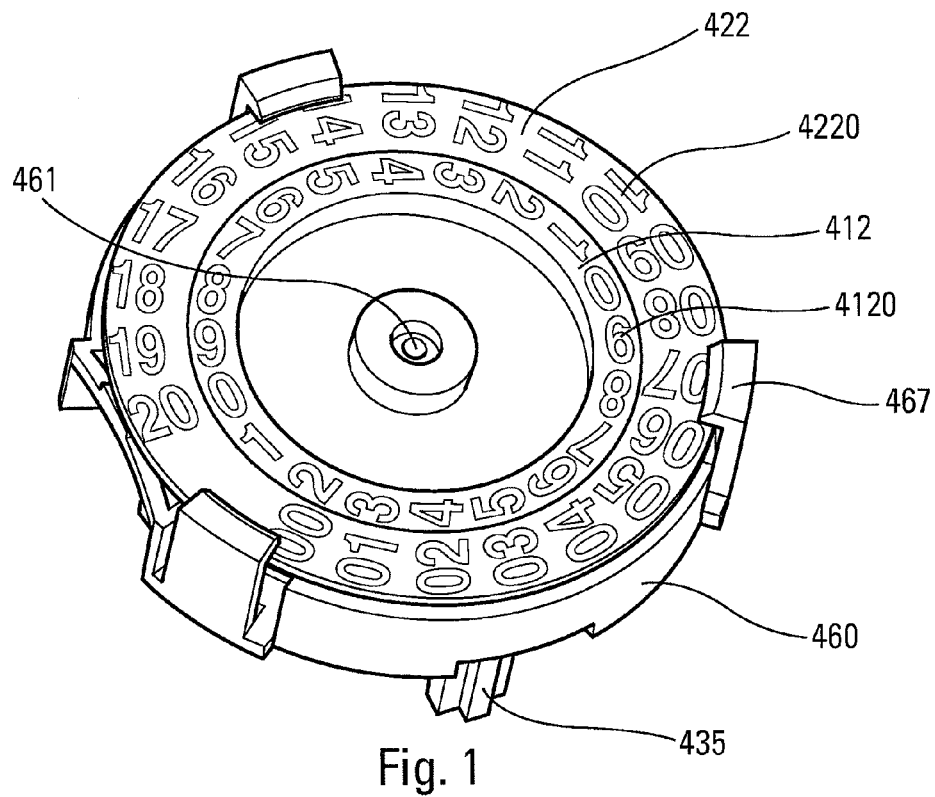
FIG. 1 is a diagrammatic perspective view from in front of a counter, in an advantageous embodiment of the present invention.
Figure 2:
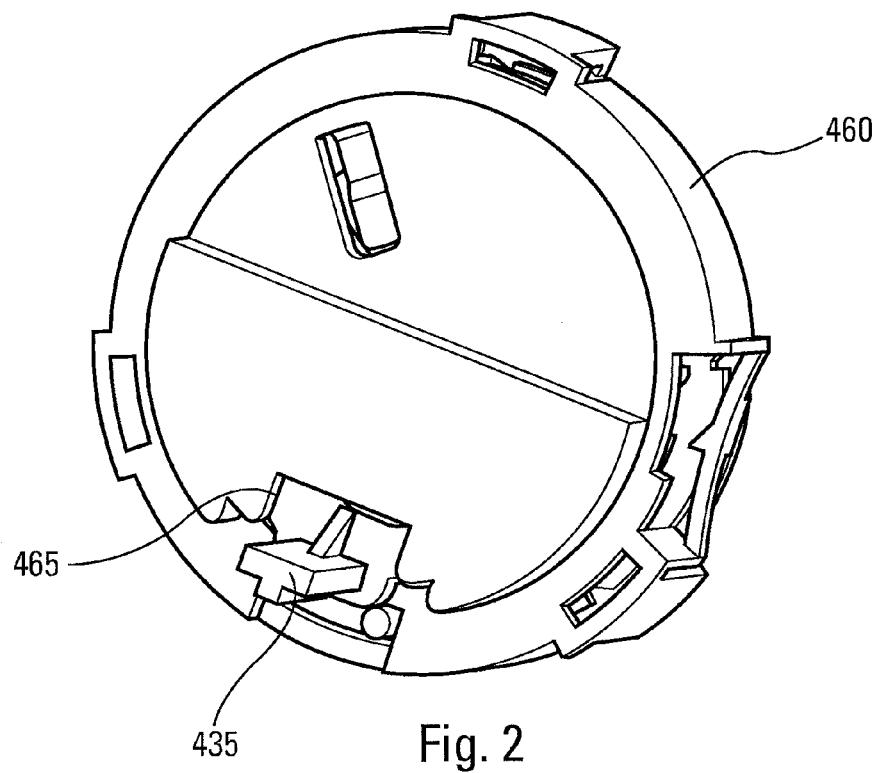
FIG. 2 is a view similar to the view in FIG. 1, but as seen from behind.
Figure 3:
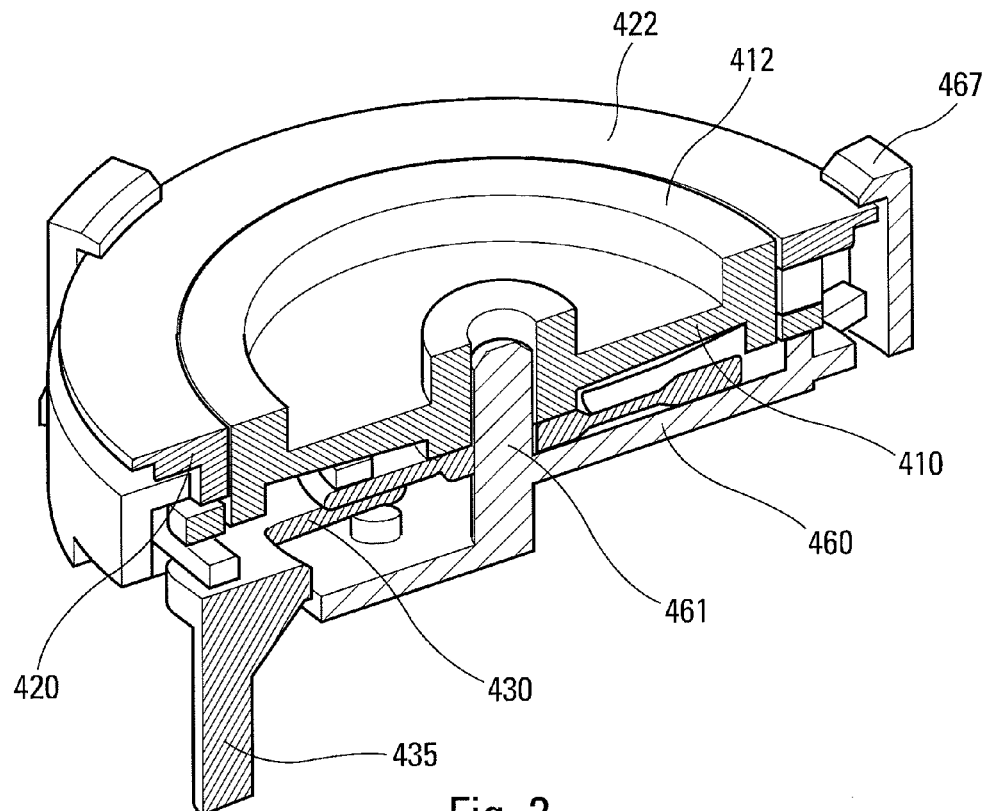
FIG. 3 is a diagrammatic perspective view partially in section of the two rotary counter elements, in an advantageous embodiment of the invention, the intermediate element being in the assembled position.
Figure 4:
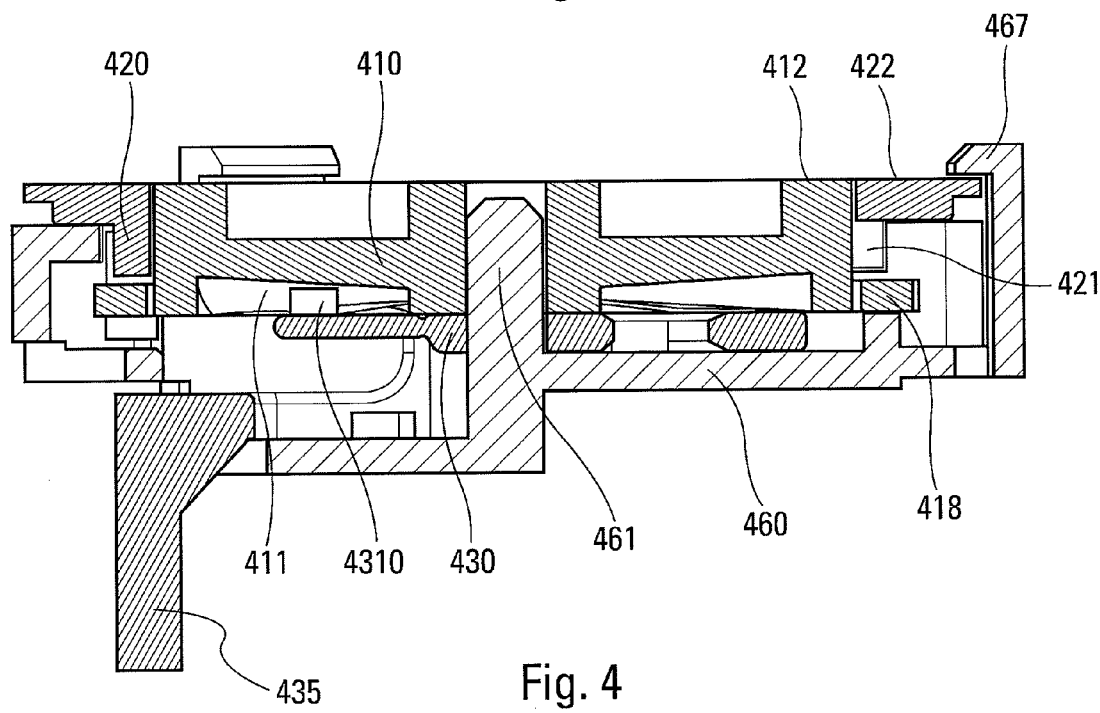
FIG. 4 is a diagrammatic cross-section view of the FIG. 3 counter.

The counter of the present invention is applicable to any type of fluid or powder dispenser, but, more particularly, it applies to a dispenser device of the MDI type (not shown), in particular it is applied to its front main face. This type of device generally includes a body that is provided with a mouthpiece that defines a dispenser orifice. A reservoir is assembled in said body, said reservoir including a metering valve that is mounted on its opening. Inside said body, the metering valve co-operates with an expulsion channel that leads into the mouthpiece. When the user presses on the bottom of the reservoir, said reservoir slides axially inside the body, causing the valve to be actuated and a dose of fluid to be expelled. The operation of such an MDI-type device is well known to the person skilled in the art, and is therefore not described more fully below. The counter may be interposed between the front main face of said body and a covering member that includes a window, and that may serve to fasten the counter on the body. Naturally, this embodiment is only an example, and, by way of example, the counter could be fastened directly to the body, independently of the presence of a covering member. The counter includes an actuator element 435 (visible in FIGS. 3 to 6) that projects out from said counter, and that is adapted to penetrate inside the body through an opening that is provided for this purpose, so as to co-operate with the reservoir or with a portion that is secured to said reservoir. In this way, each time the dispenser device is actuated, the axial movement of the reservoir in the body causes the actuator element to move axially.

The counter of the invention includes two rotary counter elements, namely a first rotary counter element 410, shown in detail in FIGS. 8a and 8b, and a second rotary counter element 420, shown in detail in FIGS. 7a and 7b, and an actuator member 430. The actuator member 430 that includes the actuator element 435, is for transforming an axial movement of a portion of the dispenser device, generally the reservoir, into a turning movement of the first counter element 410.

In a preferred variant embodiment the counter is disposed on a face of the body of the dispenser device, and the actuator member 430 thus transforms an axial movement of the reservoir, along the axis of the reservoir, into a turning movement of the first counter element 410. In this configuration, the two rotary elements 410, 420, of the counter turn about a pivot pin 461 that is substantially perpendicular to the axial movement. Advantageously, the actuation cycle of the counter may start at the very beginning of the stroke of the reservoir, such that the counter is actuated before any fluid is dispensed.

The first rotary counter element 410 forms the units wheel, and the second rotary counter element 420 forms the tens wheel, said first and second counter elements co-operating with each other to define and to display, in a viewing window (not shown), the number of doses of fluid that have been dispensed or that remain to be dispensed from said reservoir. Preferably, this number is formed by a display zone in which the number is displayed horizontally when the dispenser device is in its normal working position in which the body is substantially vertical with the mouthpiece disposed at the bottom. Said first counter element 410 co-operates with the actuator member 430 that is adapted to cause said first counter element 410 to turn each time said actuator member is actuated. Interconnection means are adapted to cause said second counter element 420 to turn on every tenth actuation of said actuator member 430, and thus on every tenth turn of said first counter element 410. Both counter elements are advantageously assembled in rotary manner around the same pivot pin 461.

As shown in FIGS. 1 to 6, the counter preferably includes a base body 460 to which a lid (not shown) may be associated. Said base body forms the pivot pin 461, and includes an opening 465 through which the actuator element 435 is able to pass. The lid may include a viewing window enabling the user to see the display zone that is formed jointly by said first and second counter elements 410, 420. The base body 460 may include fastener means 467, such as snap-fastener tabs, that are adapted to fasten the outer edge of the second counter element 420, without however limiting its capacity to turn about its pin 461. The second counter element 420 retains the first counter element 410 that in turn retains the actuator member 430 in the base body 460. Thus, said counter may advantageously be pre-assembled so as to form a counter unit, said counter unit possibly including fastener means for fastening to the body of the fluid dispenser device.

As shown in FIGS. 8a and 8b, said first counter element 410 may include a first peripheral set of teeth 411, which set, on each actuation, co-operates with a flexible actuator tab 431 of the actuator member 430. Advantageously, said first counter element 410 is substantially disk shaped, being provided with a central through opening 415 that is adapted to be engaged around its pivot pin 461. The top face of said disk includes a first peripheral edge portion 412 that receives counter indices 4120, such as one or more series of numbers from 0 to 9. The example shown in FIG. 1 shows two series of numbers from 0 to 9, distributed over said periphery. The bottom face of said disk includes said first peripheral set of teeth 411, as can be seen in FIG. 8b. Preferably, the teeth of the first set of teeth 411 are oriented axially. As visible in FIG. 8a, the top face of said first counter element 410 may include a central plane portion that surrounds the central opening 415 and that is extended radially outwards by said first peripheral edge portion 412 that is raised axially relative to said central portion. The peripheral edge portion 412 is extended radially outwards by an outer plane portion 413 that does not extend over the entire periphery, but that is interrupted by at least one, preferably two, flexible tabs 418 each of which includes a respective lug 419 at its end. The flexible tabs 418 extend in peripheral manner, and the lug 419 may extend perpendicularly to its respective tab 418, as visible in FIGS. 8a and 8b. This embodiment makes it possible to superpose the second counter element 420 on the first counter element 410 with an overall thickness that is small.

As shown in FIGS. 7a and 7b, said second counter element 420 may include a second peripheral set of teeth 421, which set is adapted, on every tenth actuation of the actuator member 430, to co-operate with a lug 419 of said first counter element 410. Advantageously, said second counter element is substantially ring shaped, adapted to be disposed on said outer portion 413 of said first counter element 410. The top face of said ring includes a second radially-outer peripheral edge portion 422 that receives counter indices 4220, such as the numbers from 00 to 20, distributed over said periphery. In this example, the counter is thus capable of counting 200 doses. The bottom face of said ring includes said second peripheral set of teeth 421, disposed radially inside, and extending axially downwards, and a third peripheral set of teeth 426, disposed radially outside said bottom face. The third set of teeth 426 is adapted to co-operate with at least one projection that is provided on the base body 460 so as to act as non-return means. Advantageously, after assembling the first and second counter elements 410, 420 around their common pivot pin 461, said second peripheral edge portion 422 of said second counter element 420 is disposed radially outside, and substantially in contact with, said first peripheral edge portion 412 of said first counter element 410, the top surfaces of said first and second peripheral edge portions 412, 422 being substantially in alignment or coplanar, so as to form the display zone that is visible through the viewing window.

The first counter element 410 includes at least one deformable finger 418, preferably two diametrically-opposite fingers, the deformable finger(s) being adapted, on every tenth actuation, to co-operate with a cam that is secured to the base body. A plurality of cams may optionally be provided. The second set of teeth 421 of the second counter element 420 is for co-operating with the lug 419 of a deformable finger 418 of the first counter element each time said deformable finger is moved towards its deformed position by said cam. More clearly, the cam provided in said base body is adapted to deform a deformable finger 418 resiliently and radially inwards, each time the lug 419 of said deformable finger 418 co-operates with said cam. When the finger 418 is not deformed, said lug 419 does not co-operate with said second set of teeth 421.

In the example shown in the drawings, the first counter element 410 includes two diametrically-opposite fingers 418, and two series of numbers from 0 to 9, distributed over the periphery. On every tenth actuation, one of the two deformable fingers 418 co-operates with said cam, preferably provided radially on the outside relative to said fingers, so as to deform them inwards and enable said lug 419 to co-operate with the second set of teeth 421 of the second counter element 420. The second counter element 420 is thus also turned. The third set of teeth 426 of the second counter element 420 is for co-operating with non-return means, e.g. a projection that may be secured to the base body 460. It should be noted that the non-return means could equally well co-operate with the second set of teeth, in which situation the second counter element 420 could include a single set of teeth only.

An advantage of the counter of the present invention is that it makes a large display possible, without increasing the bulkiness of the counter. In particular, the embodiment shown makes it possible for a 200-dose counter to display numbers (firstly units, secondly tens) having a height that is greater than 2 mm, preferably about 2.5 mm, and a width that is greater than 1.5 mm, preferably about 2 mm. This represents an increase in the physical size of the numbers of up to 50% relative to existing counters.

In the embodiment shown, the indicator is adapted to indicate the number of doses that remain to be dispensed, such that the number displayed decreases on each actuation. Naturally, the inverse is also possible, namely a counter that counts the number of doses that have been dispensed.

Figure 5:
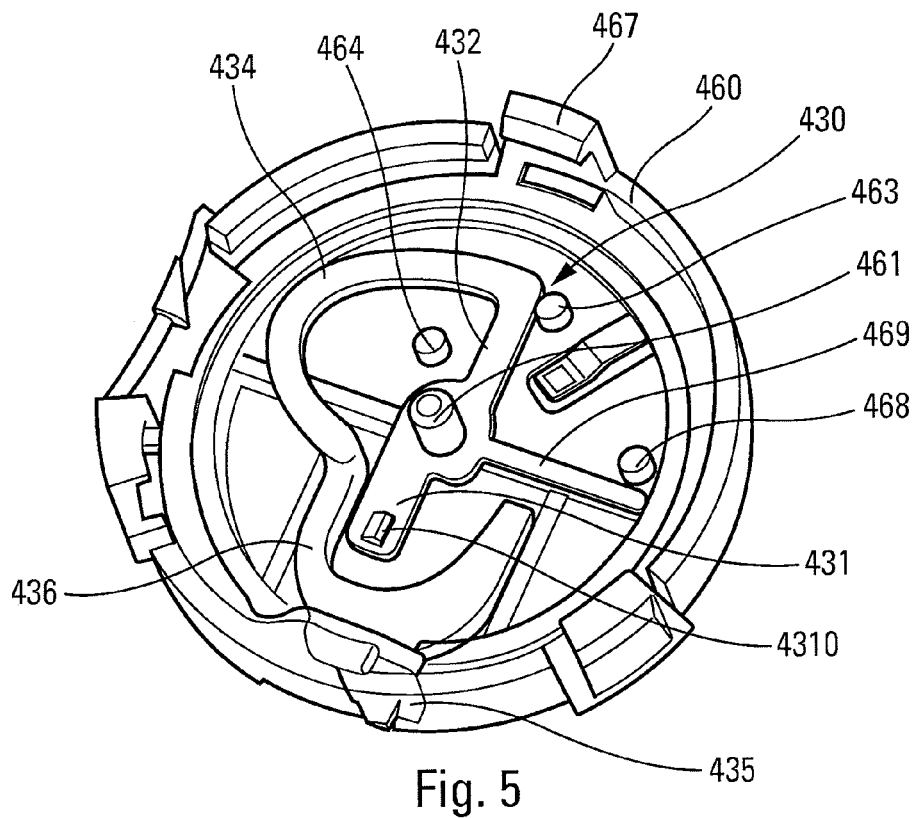
FIG. 5 is a partially-transparent diagrammatic perspective view from in front of the actuator member of the counter, in an advantageous embodiment, shown assembled in the base body.
Figure 6:
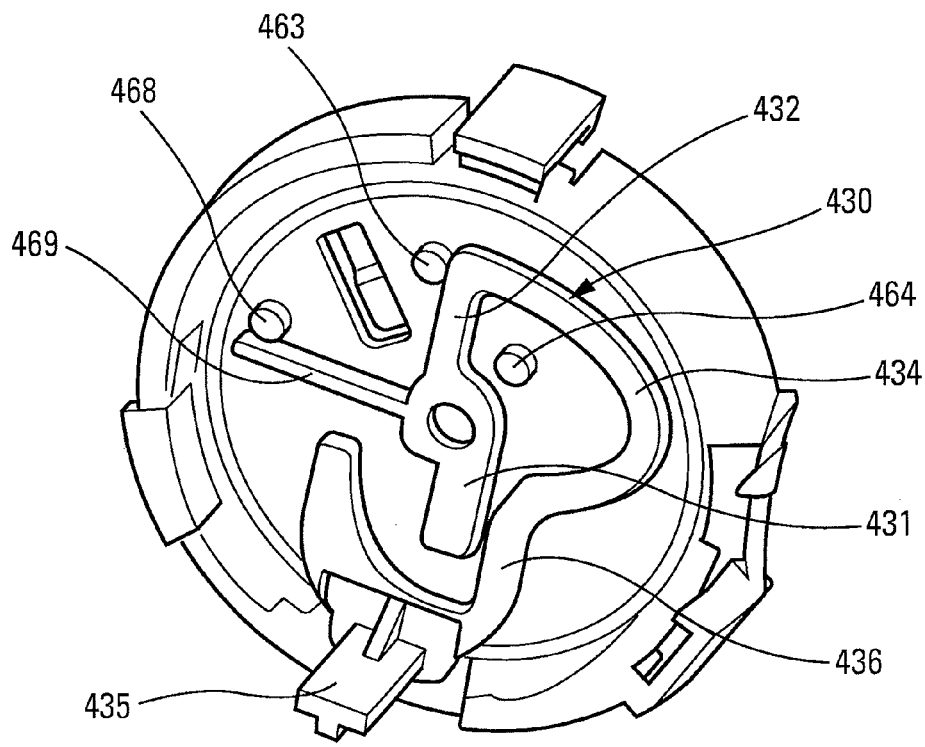
FIG. 6 is a view similar to the view in FIG. 5, but as seen from behind.

Advantageously, said actuator member 430 is assembled in said base body 460 by being engaged around the pivot pin 461, in particular as visible in FIGS. 5 and 6. The actuator member includes a tab 431 that supports a lug 4310 that is adapted to co-operate with the first set of teeth 411 of the first counter element 410. The tab 431 may extend radially downwards from the pivot pin 461, when the counter is in its normal vertical working position. However, it could equally well extend in another direction, e.g. horizontally in the working position. The tab 431 is extended on another side of the pivot pin 461 by a substantially rigid rectilinear radial portion 432, itself connected to an elastically-deformable portion 434 forming a loop making it possible to pass around the pivot pin 461. The elastically-deformable portion 434 is extended by a rigid support portion 436 that supports the actuator element 435 that is movable in the same direction as the reservoir with which it co-operates. Advantageously, abutment means 463, 464 are provided so as to form an abutment to the turning movement of the tab 431. The abutment means may advantageously be formed by two projections 463, 464 from the base body 460 that may co-operate with the substantially rigid rectilinear portion 432 that extends the tab 431 on the other side of the pivot pin 461 in the embodiment shown in the figures. Other abutment means could also be envisaged. Thus, on each actuation, the actuator element 435 is moved downwards into the position in FIG. 6, causing the tab 431 to turn around the pivot pin 461. When the abutment position of the tab 431 is reached, the actuator element 435 can continue its rectilinear movement by means of the elastically-deformable portion 434. Advantageously, the tab 431 is substantially rigid, but is flexible in a direction that is perpendicular to the plane of the base body 460. This enables the tab 431 to deform a little so as to enable the lug 4310 to slide over the set of teeth 411 and engage in the next tooth. Advantageously, the actuator member 430 includes resilient means 469, such as a resilient blade that co-operates with an appropriate shoulder 468 of the base body 460, so as to form a return spring for the actuator member 430. In the embodiment shown, the resilient blade 469 extends perpendicularly to the flexible tab 431. Naturally, if the flexible tab 431 extended in another direction (e.g. the direction of the resilient blade 469 in FIG. 5), then the resilient blade would also extend in another direction. In particular, the resilient blade 469 and the flexible tab 431 could be inverted relative to the configuration in FIGS. 5 and 6. The axially deformable portion 434 of the actuator member 430 that supports the actuator element 435 makes it possible to continue the rectilinear movement of the actuator element 435 (and thus of the reservoir) after the abutment position of the tab 431 defined by the projection has been reached. The abutment may be formed such that a turn of exactly one tooth is obtained when the abutment position is reached. Since the actuation of the valve generally requires a greater stroke, and thus a greater axial movement of the reservoir along the axis of the reservoir, the deformable portion 434 of the actuator member 430 makes it possible to continue the axial movement of the reservoir to its full stroke. In addition, the system makes it possible to actuate the counter before beginning to dispense the fluid.

As a result of its components and of the arrangement of said components relative to one another, the counter of the invention thus makes it possible to make a counter that may be pre-assembled so as to form a counter unit, and that presents, in its pre-assembled state, a very small thickness, typically less than or equal to 7 mm, advantageously less than 6 mm, and possibly even less than 5 mm.

Various modifications may also be envisaged by a person skilled in the art, without going beyond the ambit of the present invention, as defined by the accompanying claims.

The invention claimed is:

1. A dose counter for counting the number of doses of fluid or powder that have been dispensed or that remain to be dispensed from a fluid dispenser device, said counter including a first rotary counter element (410) forming a units wheel, and a second rotary counter element (420) forming a tens wheel, said first and second counter elements (410; 420) co-operating with each other to define said number of doses, said first counter element (410) co-operating with an actuator member (430) that is adapted to cause said first counter element (410) to turn each time said actuator member (430) is actuated, said first rotary counter element (410) including means (418, 419) that are adapted to cause said second counter element (420) to turn on every tenth actuation of said actuator member (430), said first and second counter elements (410; 420) turning about a common pivot pin (461), said counter being characterized in that said actuator member (430) includes an opening that is mounted in rotary manner on said pivot pin (461), a substantially rigid and substantially rectilinear tab (431) extending radially from said opening, said tab (431) supporting a lug (4310) that is adapted to co-operate with the first counter element (410) on each actuation, said tab (431) being extended on another side of said pivot pin by a substantially rigid and substantially rectilinear portion (432) that extends radially from said opening, and that is connected to an elastically-deformable portion (434) of shape that is curved and that passes, at least in part, around the pivot pin (461), said deformable portion (434) being extended by a support portion (436) that is substantially rigid and that supports an actuator element (435), such that, on each actuation, said actuator element (435) is moved in translation and transmits this traction force to said elastically-deformable curved portion (434), causing said rectilinear portion (432) and said tab (431) to turn about said pivot pin (461).

2. A counter according to claim 1, wherein abutment means (463, 464) define the maximum turning amplitude of said tab (431).

3. A counter according to claim 1, wherein said support portion (436) that supports the actuator element (435) is substantially U-shaped, the two branches of the U shape surrounding said tab (431).

4. A counter according to claim 1, wherein the actuator member includes a resilient blade (469) that co-operates with a projection (468) so as to form resilient return means that return the actuator member (430) into its rest position, after each actuation.

5. A counter according to claim 4, wherein the flexibility of said resilient blade is greater than the flexibility of said elastically-deformable curved portion (434), such that, during actuation, the actuator member (430) firstly turns around the pivot pin (461), so as to cause the first counter element (410) to turn, and then the actuator element (435) is free to continue its axial movement by means of said elastically-deformable portion (434) deforming.

6. A counter according to claim 1, wherein the counter includes a base body (460) that incorporates the pivot pin (461) and an opening (465).

7. A counter according to claim 6, wherein said base body (460) includes fastener means (467), such as snap-fastener tabs, for holding the actuator member (430) and the first and second counter elements (410, 420) assembled on said base body, said counter possibly being pre-assembled so as to form a counter unit, said counter unit including fastener means for fastening to a body of a fluid dispenser device.

8. A counter according to claim 1, comprising:

a first rotary counter element (410) provided with a first peripheral edge portion (412) including counter indices (4120), such as one or more series of numbers from 0 to 9, in particular two series of numbers from 0 to 9, distributed over said periphery, and provided with a first set of teeth (411);

a second rotary counter element (420) provided with a second peripheral edge portion (422) including counter indices (4220), such as numbers from 00 to 20, distributed over said periphery, and provided with a second set of teeth (421) and with a third set of teeth (426); and a movable actuator member (430) that is movable between a first position and a second position, said actuator member including a tab (431) that is adapted to co-operate with said first set of teeth (411) of said first counter element (410), so as to cause said first counter element (410) to turn when said actuator element (430) is moved from its first position to its second position;

said first counter element (410) including at least one deformable finger (418) that is movable between a non-deformed position and a deformed position, which deformable finger is adapted, in its deformed position, to co-operate with said second set of teeth (421) of said second counter element (420), so as to cause said second counter element (420) to turn;

said counter including a base body (460) that supports said actuator member (430) and said first and second counter elements (410, 420), said base body including a cam that is adapted to deform said at least one deformable finger (418) towards its deformed position.

9. A counter according to claim 1, wherein said second peripheral edge portion (422) of said second counter element (420) is coplanar with, and radially outside, said first peripheral edge portion (412) of said counter element (410), said first and second counter elements (410, 420) having a common axis.

10. A counter according to claim 1, wherein said first rotary counter element (410) includes two deformable fingers (418) that are diametrally opposite each other on said first counter element (140).

11. A counter according to claim 10, wherein said first counter element (410) is a disk, said deformable fingers (418) being disposed at 180° from each other and co-operating with a cam that is disposed radially on the outside of said disk, so that when a deformable finger (418) co-operates with said cam, it is deformed radially inwards into its deformed position, so as to come into engagement with said second set of teeth (421) of said second counter element (420).

12. A fluid or powder dispenser device comprising a reservoir, a dispenser member, such as a metering valve, that is mounted on said reservoir, and a body incorporating a dispenser orifice, said reservoir being movable in said body so as to dispense the fluid or powder, said dispenser device being characterized in that it includes a counter according to claim 1.

13. A device according to claim 12, wherein said counter is fastened on a face of the body, said device being actuated by the user pressing axially on the reservoir, and said counter being actuated by said axial movement of said reservoir that co-operates with said actuator element (435) of the actuator member (430).

* * * * *